Jan. 9, 1968 P. K. REINERO ETAL Plant Pat. 2,788
ALMOND TREE
Filed Nov. 2, 1966
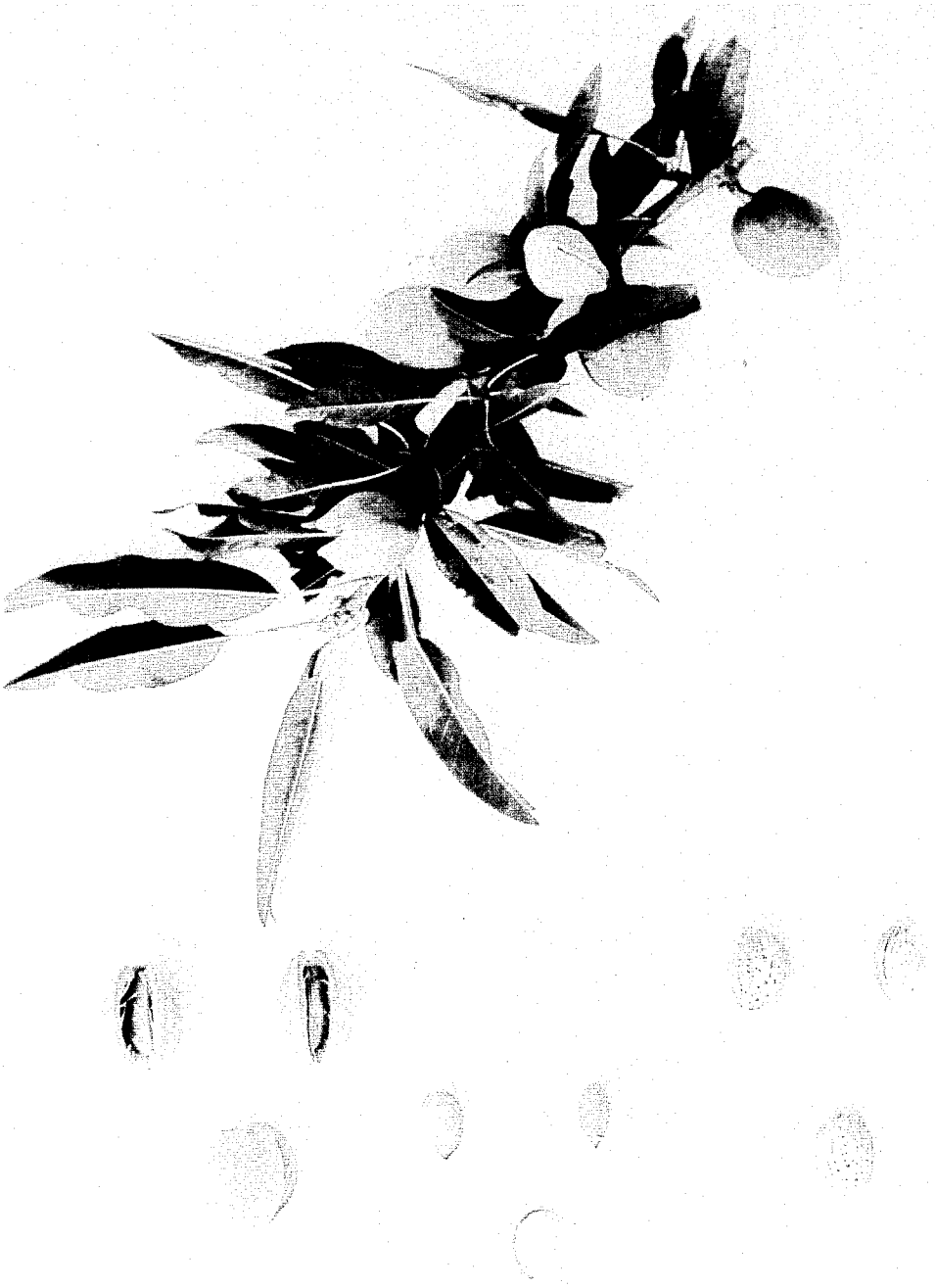
INVENTORS
Peter K. Reinero
Adolph J. Reinero
BY
Webster & Webster
ATTORNEYS United States Patent Office Plant Pat. 2,788
Patented Jan. 9, 1968

2,788
ALMOND TREE

Peter K. Reinero and Adolph J. Reinero, Merced, Calif., assignors to Reinero Brothers, Winton, Calif., a partnership Filed Nov. 2, 1966, Ser. No. 591,663
1 Claim. (Cl. Plt.—30)

This discovery relates to a new and distinct variety of almond tree which is a vigorous grower and a regular and heavy bearer of commercially desirable nuts.

While generally resembling the Davey (unpatented) in tree and nut characteristics, the present variety is distinct in a number of respects.

More particularly, and in comparison with the Davey, the herein claimed variety of almond tree begins to bear commercial crops in the fourth year and about two years before the Davey, is a more vigorous grower with darker green foliage, blooms about two days later, and is in harvest about twelve days later.

In additional comparison, the nuts of the herein claimed variety knock much easier, the pits are larger and more numerous, the streak is shorter, broader, and darker, and the wing is broader.

In further comparison, the kernel is wider in relation to length, and more rounded in shape with a more obtuse apex, and a larger stem scar; the kernel being less wrinkled with slightly more pubescence, and has a darker, thicker pellicle.

In still further comparison, the nuts on young trees are clustered on the lower limbs rather than scattered over the tree as on young trees of the Davey.

The present variety of almond tree was discovered by us growing as a chance seedling on our ranch located near Winton, Merced County, Calif.; it being surmised that the variety is an open pollinated seedling of the Nonpareil (unpatented). When such seedling grew to maturity, and—under continuing observation—we recognized its novel characteristics (including the vigorous growth and regular production of heavy crops), asexual reproduction of the variety was accomplished as follows:

Upon our behalf a commercial nursery of Reedley, Fresno County, Calif., budded a substantial number of Nonpareil rootstock with buds from the original tree of the instant variety, and such trees were planted and grown on our ranch located near Merced, Merced County, Calif.; such reproductions in maturity having run true to the original tree in all respects.

The drawing is an illustration, by photographic reproduction in color, and at the time of harvest, of a twig with attached nuts; the drawing also showing certain of the nuts detached and both in and out of hull. Additionally, the drawing shows several of the kernels, with one cut to expose the meat.

Referring now more specifically to the botanical details of this new and distinct variety of almond tree, the following is an outline description thereof; all major color plate identifications being by reference to Maerz and Paul Dictionary of Color; except where common terms of color definition are employed:

Tree:
- *Density.*—Open.
- *Size.*—Large.
- *Vigor.*—Vigorous.

Trunk:
- *Form.*—Medium.
- *Texture.*—Medium.

Branches:
- *Form.*—Medium.
- *Texture.*—Smooth.
- *Lenticels.*—Numerous; large but variable.

- *Branching habit.*—Upright. Similar to Davey, more than Nonpareil, but less than Mission (unpatented).
- *Color.*—New wood—light green, dull. Mature wood—brown, dull.

Foliage: Quantity—medium.

Leaves:
- *Size.*—Large. Average length—93 mm. Average width—29 mm.
- *Shape.*—Ovate; acutely pointed.
- *Thickness.*—Medium.
- *Texture.*—Smooth.
- *Margin.*—Finely crenate.
- *Petiole.*—Length—long; average, 24 mm.
- *Glands.*—Number—2 to 6, occasionally 8. Alternate; large; globose. Green—occasionally reddish-brown. Positioned on base of blade and petiole.
- *Stipules.*—Present, but minute.
- *Color.*—Top side—Dull Forest Green (23–L–6). Under side—Dull Spinach Green (22–K–7).

Bloom:
- *Amount of bloom.*—Average.
- *Color.*—White.
- *Blooming period.*—Medium, as compared to other varieties; i.e. 11 days earlier than Texas (unpatented), and about 2 days later than Nonpareil and Davey.

Crop:
- *Bearing.*—Regular bearer.
- *Productivity.*—Heavy.
- *Distribution of nuts on mature tree.*—Well distributed.
- *Harvest period.*—Medium, as compared to other varieties; i.e. about 12 days after Davey, and 14 days after Nonpareil.
- *Tenacity.*—Hangs well on tree. Easy to harvest—knocks easier than Davey. Easy to hull—similar to Davey and Nonpareil.

Hull:
- *Outer surface.*—Smooth.
- *Form.*—Regular.
- *Thickness.*—Thin.
- *Flesh.*—Tough.
- *Suture.*—Ridged, with slight ventral suture depression on ridge.
- *Color.*—Silver Green (21–I–3).
- *Pubescence.*—Medium.
- *Dehiscence.*—Opens freely.
- *Splitting.*—Along suture.

Nut:
- *Size.*—Medium. Average length—30 mm. Average width—20.3 mm. Average thickness—15 mm. Average weight—2.02 grams.
- *Form.*—Length / width—ovate. Width / thickness—medium.
- *Shell.*—Soft. Outer shell—crumbling. Inner shell—well sealed.
- *Color.*—Light Straw (11–H–4).
- *Pits.*—Large; numerous; deep; round.
- *Base.*—Ventrally oblique.
- *Stem scar.*—Small. Obtuse—ventrally sloping.
- *Apex.*—Obtuse; sharp.
- *Wing.*—Broad; thin; tapered toward base.
- *Inner surface.*—Medium colored.
- *Ventral streak.*—Light; narrow; long; point acute; corky.
- *Percentage of kernel to nut.*—58%.

Kernel:
- *Size.*—Large. Average length—21.0 mm. Average width—13.4 mm. Average thickness—8.5 mm.
- *Kernel per ounce on average sample.*—12.6.

*Form.*—Length / width—ovate. Width / thickness—medium.
*Base.*—Ventrally oblique.
*Stem scar.*—Small; obtuse.
*Apex.*—Acute.
*Plumpness.*—Smooth.
*Pellicle.*—Thin.
*Pubescence.*—Smooth.
*Color.*—Indian Tan (13–I–8).
*Number of doubles.*—Few.
*Defective kernels.*—Very few.
*Flavor.*—Dry; sweet.
*Quality.*—Very good.

The tree and its nuts herein described may vary in slight detail due to climatic and soil conditions under which this variety may be grown; the present description being of the variety as grown in the Central Valley of California.

The following is claimed:

1. A new and distinct variety of almond tree, substantially as illustrated and described, which is a vigorous grower and a regular and heavy producer, and while bearing general resemblance in tree and nuts to the Davey is, in comparison, characterized as to novelty by more vigorous growth with darker green foliage, bears a crop approximately two years earlier, blooms about two days later, and is in harvest about twelve days later; and in further comparison is characterized by medium size nuts which knock easier, and nuts wherein the pits are larger and more numerous, the streak is shorter, broader, and darker, the wing is broader, and the kernel is wider in relation to length and more rounded in shape with a more obtuse apex.

No references cited.

ROBERT E. BAGWILL, *Primary Examiner.*